US008465431B2

United States Patent
Daft et al.

(10) Patent No.: US 8,465,431 B2
(45) Date of Patent: *Jun. 18, 2013

(54) MULTI-DIMENSIONAL CMUT ARRAY WITH INTEGRATED BEAMFORMATION

(75) Inventors: Christopher M. W. Daft, Pleasanton, CA (US); D-L Donald Liu, Issaquah, WA (US); Paul A. Wagner, San Carlos, CA (US); Igal Ladabaum, San Carlos, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1336 days.

This patent is subject to a terminal disclaimer.

(21) Appl. No.: 11/788,614

(22) Filed: Apr. 20, 2007

(65) Prior Publication Data

US 2007/0242567 A1 Oct. 18, 2007

Related U.S. Application Data

(63) Continuation-in-part of application No. 11/295,794, filed on Dec. 7, 2005, now Pat. No. 7,963,919.

(60) Provisional application No. 60/795,407, filed on Apr. 26, 2006.

(51) Int. Cl.
*A61B 8/08* (2006.01)

(52) U.S. Cl.
USPC .......................................................... 600/459

(58) Field of Classification Search
USPC ................. 600/437, 443, 459; 310/317, 318, 310/334, 364; 381/190, 191; 73/602, 621, 73/642
See application file for complete search history.

(56) References Cited

U.S. PATENT DOCUMENTS

| 4,204,435 | A |   | 5/1980  | Bridoux et al.         |
|-----------|---|---|---------|------------------------|
| 4,793,184 | A | * | 12/1988 | Ikeda et al. ... 73/626 |
| 4,817,434 | A |   | 4/1989  | Anderson               |
| 5,186,175 | A | * | 2/1993  | Hirama et al. ... 600/447 |
| 5,389,848 | A |   | 2/1995  | Trzaskos               |
| 5,744,898 | A |   | 4/1998  | Smith et al.           |
| 5,851,187 | A |   | 12/1998 | Thomas et al.          |
| 5,860,926 | A |   | 1/1999  | Barabash et al.        |
| 5,901,708 | A |   | 5/1999  | Chang et al.           |

(Continued)

FOREIGN PATENT DOCUMENTS

| EP | 1300690 | 4/2003 |
| EP | 1194920 | 7/2003 |

(Continued)

OTHER PUBLICATIONS

Oralkan et al. Volumetric Ultrasound Imaging Using 2D CMUT Arrays. IEEE Transactions on Ultrasonics, Ferroelectrics and Frequency Control. 50(11):1581-1595. Nov. 2003.*

(Continued)

*Primary Examiner* — Parikha Mehta

(57) ABSTRACT

To generate information representing a volume, co-arrays or synthetic transmit aperture process is performed in one dimension and beamforming is performed in another dimension. For example, a transmit aperture focuses in azimuth, but is unfocused or divergent in elevation. A multi-dimensional array receives reflected echoes. The echoes are beamformed for sub-arrays for focus in azimuth. The resulting partial beamformed information is provided to an imaging system from the probe housing for completion of beamforming at least in elevation.

23 Claims, 7 Drawing Sheets

U.S. PATENT DOCUMENTS

| | | | |
|---|---|---|---|
| 5,938,612 | A | 8/1999 | Kline-Schoder et al. |
| 5,993,390 | A | 11/1999 | Savord et al. |
| 5,997,479 | A * | 12/1999 | Savord et al. |
| 6,013,032 | A | 1/2000 | Savord |
| 6,048,315 | A | 4/2000 | Chiao et al. |
| 6,126,602 | A | 10/2000 | Savord et al. |
| 6,138,513 | A | 10/2000 | Barabash et al. |
| 6,159,153 | A | 12/2000 | Dubberstein et al. |
| 6,206,833 | B1 | 3/2001 | Christopher |
| 6,208,189 | B1 | 3/2001 | Freeman et al. |
| 6,251,073 | B1 | 6/2001 | Imran et al. |
| 6,309,356 | B1 | 10/2001 | Ustuner et al. |
| 6,352,510 | B1 | 3/2002 | Barabash et al. |
| 6,368,276 | B1 | 4/2002 | Bullis |
| 6,380,766 | B2 | 4/2002 | Savord |
| 6,385,474 | B1 | 5/2002 | Rather et al. |
| 6,491,634 | B1 | 12/2002 | Leavitt et al. |
| 6,500,123 | B1 | 12/2002 | Holloway et al. |
| 6,506,160 | B1 | 1/2003 | Van Stralen et al. |
| 6,537,219 | B2 | 3/2003 | Poland et al. |
| 6,537,220 | B1 | 3/2003 | Friemel et al. |
| 6,551,246 | B1 | 4/2003 | Ustuner et al. |
| 6,569,102 | B2 | 5/2003 | Imran et al. |
| 6,605,043 | B1 | 8/2003 | Dreschel et al. |
| 6,676,602 | B1 | 1/2004 | Barnes et al. |
| 6,783,497 | B2 | 8/2004 | Grenon et al. |
| 6,790,182 | B2 | 9/2004 | Eck et al. |
| 6,806,623 | B2 | 10/2004 | Petersen et al. |
| 7,199,738 | B2 | 4/2007 | Han et al. |
| 2002/0045830 | A1 | 4/2002 | Powers et al. |
| 2003/0149363 | A1 | 8/2003 | Dreschel et al. |
| 2003/0163046 | A1 | 8/2003 | Nohara et al. |
| 2003/0171676 | A1 | 9/2003 | Trahey et al. |
| 2004/0064027 | A1 | 4/2004 | Zimmermann et al. |
| 2004/0189499 | A1 * | 9/2004 | Han et al. ............ 341/143 |
| 2004/0267127 | A1 | 12/2004 | Abend et al. |
| 2005/0119575 | A1 | 6/2005 | Ladabaum et al. |
| 2005/0124882 | A1 | 6/2005 | Ladabaum et al. |
| 2005/0124884 | A1 | 6/2005 | Bolorforosh et al. |
| 2005/0148873 | A1 | 7/2005 | Petersen et al. |
| 2005/0148878 | A1 | 7/2005 | Phelps et al. |
| 2005/0154304 | A1 | 7/2005 | Robinson |
| 2005/0192499 | A1 | 9/2005 | Lazenby et al. |
| 2005/0203392 | A1 | 9/2005 | Petersen et al. |
| 2005/0215893 | A1 | 9/2005 | Barnes et al. |
| 2005/0243812 | A1 | 11/2005 | Phelps et al. |
| 2005/0261589 | A1 | 11/2005 | Daft et al. |
| 2006/0167206 | A1 | 7/2006 | Maier et al. |
| 2006/0173342 | A1 | 8/2006 | Panda et al. |
| 2006/0279174 | A1 | 12/2006 | Oliver et al. |

FOREIGN PATENT DOCUMENTS

| | | |
|---|---|---|
| EP | 1 391 875 a1 | 2/2004 |
| FR | 2 815 723 | 4/2002 |
| JP | 2001-245884 | 11/2001 |
| JP | 2005-143838 | 9/2005 |
| WO | WO 0068931 | 11/2000 |
| WO | WO 2005-115250 | 12/2005 |
| WO | WO 2006-003621 | 1/2006 |

OTHER PUBLICATIONS

Wygant et al. Integrated Ultrasonic Imaging Systems Based on CMUT Arrays: Recent Progress. 2004 IEEE Ultrasonics Symposium.*

Daft et al. Microfabricated Ultrasonic Transducers Monolithically Integrated with High Voltage Electronics. 2004 IEEE Symposium. 493-496.*

"Synthetic Transmit Aperture Imaging using Orthogonal Golay Coded Excitation," by Richard y. Chiao and Lewis J. Thomas; 2000 IEEE Ultrasonics Symposium; 4 pages.

"Optimizing Sparse Two-Dimensional Transducer Arrays Using an Effective Aperture Approach," by G. R. Lockwood and F.S. Foster; 1994 Ultrasonics Symposium; pp. 1497-1501.

"Application of Different Spatial Sampling Patterns for Sparse Array Transducer Design," by Svetoslav Ivanov Nikolov and Jorgen Arendt Jensen; Department of Information Technology, Center for Fast Ultrasound Imaging, Technical University of Denmark; Jun. 29, 1999; Ultrasonics 37 (2000); pp. 667-671.

"The Unifying Role of the Coarray in Aperture Synthesis for Coherent and Incoherent Imaging," by Ralph T. Hoctor, Member, IEEE and Saleem A. Kassam, Senior Member, IEEE; Proceedings of the IEEE, vol. 78, No. 4; Apr. 1990; pp. 735-752.

"Coarray Analysis of Wideband Pulse-Echo Imaging Systems," by Fauzia Ahmad and Saleem A. Kassam; Moore School of electrical Engineering, University of Pennsylvania, Philadelphia, PA; 1996 IEEE; pp. 3185-3188.

"Hybrid Multi/single Layer Array Transducers for Increased Signal-to-Noise Ration," by Richard L. Goldberg, et al.; 1997 IEEE Transactions on Ultrasonics, Ferroelectrics, and Frequency Control, vol. 44, No. 2; Mar. 1997; pp. 315-325.

"Zone-Based B-Mode Imaging," by David Napolitano et al.; 2003 IEEE Ultrasonics Symposium; pp. 25-28.

Excerpts from "Digital Image Processing," PIKS Inside, Third Edition by William K. Pratt; A Wiley-Interscience Publication; 2001; pp. 200-202.

Excerpts from "Algorithms, Complexity Analysis and VLSI Architectures for MPEG-4 Motion Estimation," by Peter Kuhn, Technical University of Munich, Germany; 1999 Kluwer Academic Publishers, Boston; pp. 30-31.

"Sparse Array Imaging with Spatially-Encoded Transmits", Richard Y. Chiao, et al., 1997 IEEE Ultrasonics Symposium, pp. 1679-1682.

U.S. Appl. No. 11/731,567, filed Mar. 30, 2007.

U.S. Appl. No. 11/731,568, filed Mar. 30, 2007.

Maginness, M.G., at al., "State-of-the-art in Two-Dimensional Ultrasonic Transducer Array Technology", Medical Physics vol. 3, No. 5, Sep./Oct. 1976, pp. 312-318.

* cited by examiner

MULTI-DIMENSIONAL CMUT ARRAY WITH INTEGRATED BEAMFORMATION

RELATED APPLICATIONS

The present patent document is a continuation-in-part of application Ser. No. 11/295,794 filed Dec. 7, 2005 now U.S. Pat. No. 7,963,919, and the present patent document claims the benefit of the filing date under 35 U.S.C. §119(e) of Provisional U.S. Patent Application Ser. No. 60/795,407 filed Apr. 26, 2006. All of the foregoing applications are hereby incorporated by reference.

BACKGROUND

The present embodiments relate to multi-dimensional transducer arrays. Beamforming may be provided for multi-dimensional capacitive membrane ultrasound transducer (CMUT) arrays.

Many clinical applications call for high volume acquisition rates. Two-dimensional arrays, especially for radiology, have enormous channel counts and element sizes that are unable to drive cables due to impedance mismatch. Cables for fully sampled two-dimensional arrays are impractically large.

A traditional array is limited in its frame rate by Nyquist spatial sampling and the scan area. When two-dimensional arrays that scan volumes are considered, the number of beams may often exceed 10,000. A typical volume may take several seconds to acquire. A data set representing a line of acoustic echoes is obtained from a transmitter firing. For a square transducer, if M beams are required to fill a plane, at least $M^2$ beams are needed to fill a volume. A typical beam is 2 wavelengths wide, and a typical transducer may be 200 wavelengths long, giving M=100. A typical beam requires 0.2 ms to acquire. Parallel receive beamforming can help, but the data acquisition is still too slow, especially in cardiology.

A fixed transmit focus constitutes a resolution problem. In cardiology, there is no time for more than one focal zone, so the image is out of focus in most of the image. If Z focal zones are needed to improve coherence, a total of $M^2 Z^2$ firings make up a volumetric image. For typical imaging depths, this results in a maximum imaging speed of $0.5/Z^2$ volumes per second.

Other acquisition techniques may be used. A mechanical drive may rock a one-dimensional transducer inside the probe handle. The volume may be acquired by free hand scanning a one-dimensional array, with probe position estimation performed in the imaging system or by position sensing. Beam formation may be performed in the probe handle. However, the speed of acquisition is limited by requirements of spatial beam sampling and the speed of sound in tissue. No channel information is available in the imaging system if real-time beam formation without channel data storage is performed. The only data available are the beams that are created by combining the channel data in the reconstruction algorithm. Availability of the raw channel data is important in a variety of clinical scenarios, such as phase aberration correction, motion/flow estimation, and elastography.

In a synthetic transmit aperture (STA) imager, two or more firings creates a volume data set. This can provide imaging speeds in excess of 1000 volumes per second. However, signal-to-noise ratio may suffer without advanced channel signal processing techniques.

BRIEF SUMMARY

By way of introduction, the preferred embodiments described below include methods, systems, transducer arrays, and receive beamformers for generating information for medical diagnostic ultrasound information. To generate information representing a volume, co-arrays or synthetic transmit aperture processing is performed in one dimension and traditional beamforming is performed in another dimension. For example, a transmit aperture focuses in azimuth, but is unfocused or divergent in elevation. A multi-dimensional array receives reflected echoes. The echoes are beamformed in sub-arrays for focus in azimuth. The resulting partially beamformed information is provided to an imaging system from the probe housing for completion of beamforming at least in elevation. The provisional of channel data in elevation to the imaging system provides data useful for channel based processing.

In a first aspect, a method is provided for generating ultrasound information for three-dimensional imaging. Data is beamformed in azimuth for a two-dimensional receive aperture. A transmit aperture is synthesized in elevation.

In a second aspect, an ultrasound transducer array is provided for medical diagnostic ultrasound imaging. A two-dimensional grid of capacitive membrane ultrasound transducer elements are on or within a probe housing. A plurality of receive channel circuits connect with the elements and are operable to at least partially beamform along a first dimension. The receive channel circuits are within the probe housing. At least one transmit element is separate from the elements of the two-dimensional grid. The transmit element is operable to generate a substantially unfocused beam along a second dimension different from the first dimension.

In a third aspect, a method is provided for generating ultrasound information for three-dimensional imaging. Acoustic energy focused along a first dimension and unfocused along a second dimension different than the first dimension is transmitted. Partial receive beamforming is performed in sub-arrays of elements. The partial receive beamforming forms data representing a two-dimensional plane extending along the second dimension at an angle in the first dimension. Then, beamforming is performed along the second dimension.

In a fourth aspect, an ultrasound transducer array is provided for medical diagnostic ultrasound imaging. A two-dimensional grid of capacitive membrane ultrasound transducer elements is on or within a probe housing. The elements are on or in a substrate. A plurality of sigma-delta analog-to-digital converters are on or in the substrate. A plurality of receive channel circuits connect with the converters and are operable to at least partially beamform along at least a first dimension. The receive channel circuits are on or in the substrate.

The present invention is defined by the following claims, and nothing in this section should be taken as a limitation on those claims. Further aspects and advantages of the invention are discussed below in conjunction with the preferred embodiments and may be later claimed in combinations or independently.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Integrating partial beamforming capabilities in the transducer probe housing and using synthetic transmit aperture may allow for more versatile three-dimensional imaging. A focused beam is transmitted in one dimension and an unfocused beam in the orthogonal dimension. With low-power analog-to-digital conversion, such as with sigma-delta converters, and partial beam formation, receive planes are formed for each transmit event. The cable count or bandwidth requirements for communication from the transducer probe to a computer or other imaging system are lower due to partial beam formation.

In one embodiment, a combination of synthetic aperture imaging, capacitive membrane transducers (cMUTs), and integrated electronics is provided. Synthetic aperture imaging with a fully sampled receive aperture may increase acquisition speed and allow for greater focus at all locations. Receiving data from the fully sampled array without full beamforming may allow advanced signal processing algorithms, such as phase aberration correction, vector flow, and adaptive imaging, to be provided in the imaging system.

Figure 1:
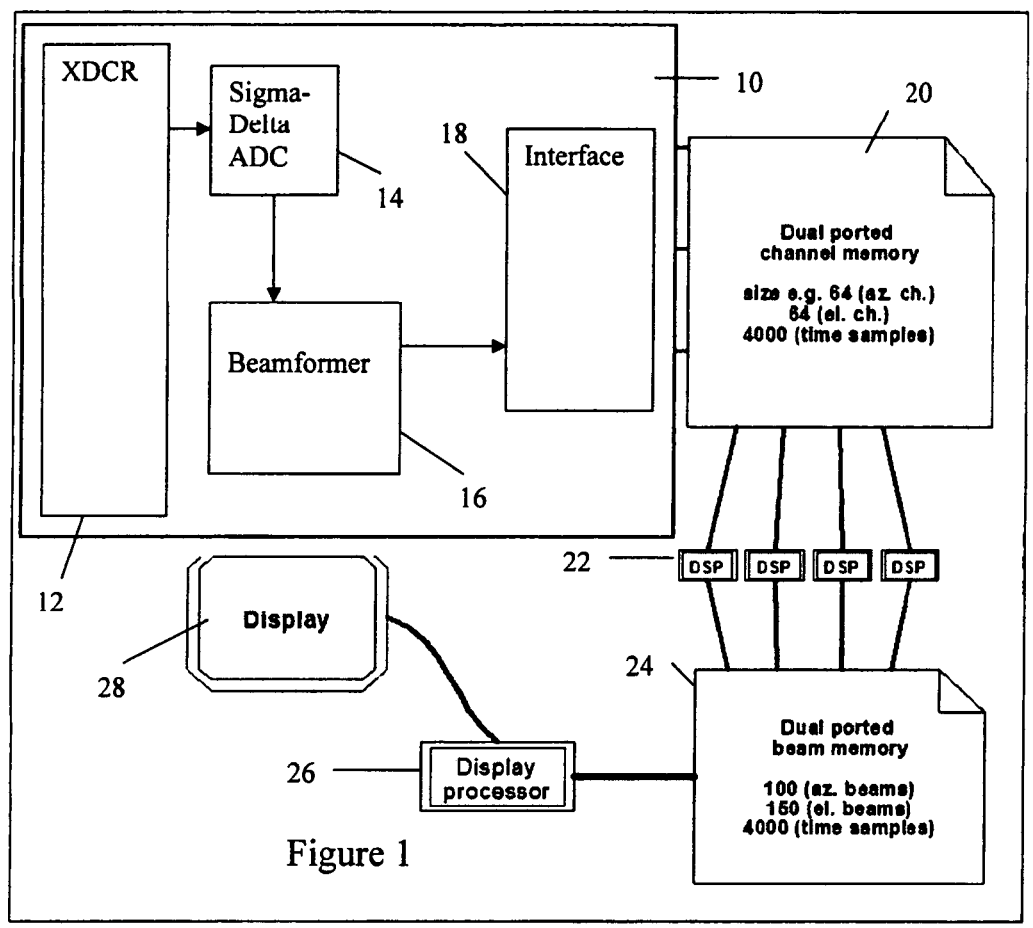
FIG. 1 is a block diagram of one embodiment of a medical diagnostic ultrasound system for three-dimensional imaging.

FIG. 1 shows an ultrasound transducer array 12 with a system for medical diagnostic ultrasound imaging. The system is for three-dimensional imaging, but may be used for two-dimensional or other ultrasound imaging. The system includes a probe housing 10 and components in an imaging or back-end system. The back-end is a medical diagnostic imager, an imaging system specifically for this overall system, a computer, or a workstation. In one embodiment, the probe housing 10 connects with a releasable transducer connector of an ultrasound imaging system. Electronics in the probe housing 10, an adaptor, and/or software in the imaging system use the partially beamformed samples for generating an image. In other embodiments, the back-end includes a bus, data input, receiver, or other device specifically for operating on data output from the probe housing 10.

The system includes the probe housing 10, the transducer array 12, analog-to-digital converters 14, a beamformer 16, an interface 18, a first memory 20, a beamformer 22, a second memory 24, a display processor 26, and a display 28. Additional, different, or fewer components may be provided. For example, the memories 20 and 24 are combined. Other separations between the probe housing 10 and the back-end may be used, such as putting the memory 20 and beamformer 22 in the probe housing.

The probe housing 10 is plastic, fiberglass, epoxy, or other now known or later developed material. The probe housing 10 includes an acoustic window to enhance patient contact and provide electrical isolation, thin region, different material region, or other portion positioned adjacent the transmitting face of the transducer array 12. The housing is shaped for handheld operation, such as providing a grip region sized and shaped for being held by a user. One or more larger regions may be provided, such as for holding the array 12. In other embodiments, the probe housing 10 is shaped for insertion within the body, such as a trans-esophageal, intra-operative, endo-cavity, catheter, or other probe shape.

The probe housing 10 encloses the transducer array 12 and other electronics, such as the analog-to-digital converters 14, beamformer 16, and interface 18. The electronics are immediately adjacent the transducer array 12 in one embodiment. For example, at least some of the electronics are formed on a same semiconductor or chip as the array 12. As another example, flip-chip bonding or other connection is provided between the array 12 and the analog-to-digital converters 14. In other embodiments, such as in a catheter, some of the electronics are spaced inches or feet from the array 12, such as the electronics being in a catheter handle. The array 12 or other electronics may be within, on, or against the probe housing 10.

The transducer array 12 is a multi-dimensional array of elements. The elements are distributed in a rectangular grid, such as N×M where N and M are greater than one and equal or unequal. Triangular, hexagonal or other distribution grids may be used. The elements are piezoelectric or capacitive membrane ultrasound transducers. Piezoelectric elements may be single crystal, ceramic blocks, multi-layer, films, or other now known or later developed transducer elements. Capacitive membrane ultrasound transducers may be formed from complete membranes, beams or other movable structure adjacent a gap for movement. The capacitance changes as the mechanical structure moves, generating electrical signals. Changes in potential may cause movement of the mechanical structure. Other now known or later developed microelectromechanical device may be used for the capacitive membrane ultrasound transducer. The cMUT is formed using any semiconductor process or another process.

The transducer array 12 includes transmit elements 30 and receive elements 32. The transmit elements 30 are of the same or different structures as the receive elements 32. For example, the transmit elements 30 are annular elements 54, and the receive elements 32 are in a regularly spaced multi-dimensional grid. As another example, the transmit elements 30 are piezoelectric, and the receive elements 32 are cMUT elements. In another example, the transmit and receive elements 30, 32 are cMUT elements formed as part of a same multi-dimensional grid.

Figure 6:
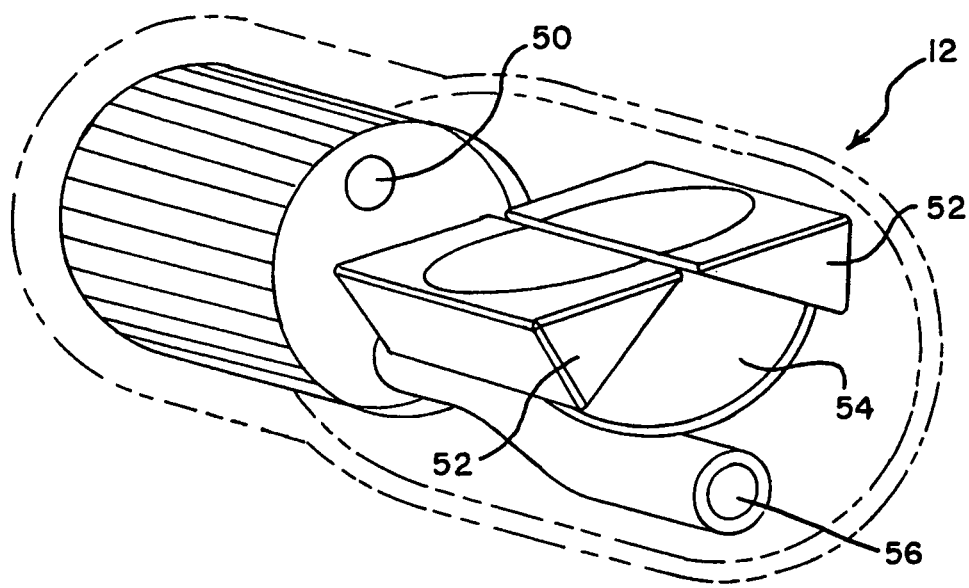
FIG. 6 is a graphical representation of a transesophageal probe according to one embodiment.

The transmit elements 30 provide for divergent beams. By defocusing or limiting a number of transmit elements 30, a larger volume may be insonified for a given transmit event. By receiving with a multi-dimensional receive aperture, a volume may be more quickly scanned. In one embodiment, the transmit elements 30 provide for focus along one dimension (e.g., azimuth) and a divergent waveform or lack of focus along another dimension (e.g., elevation). In the embodiment of FIG. 6, the transmitter provides an electronic focus in azimuth. In elevation, a tight focus is achieved by array curvature in the plane of the receiver. The beam subsequently diverges in elevation, creating a "fan beam" irradiation pattern. The dimensions may be orthogonal, acute, or have other relationships to each other. In other embodiments, the transmit elements 30 provide for divergent or volume scanning in azimuth and elevation. The divergent beams may be focused to provide a volume or plane wave scan for a specific multi-scan line volume. Beams focused in both azimuth and elevation may be used.

Figure 2:
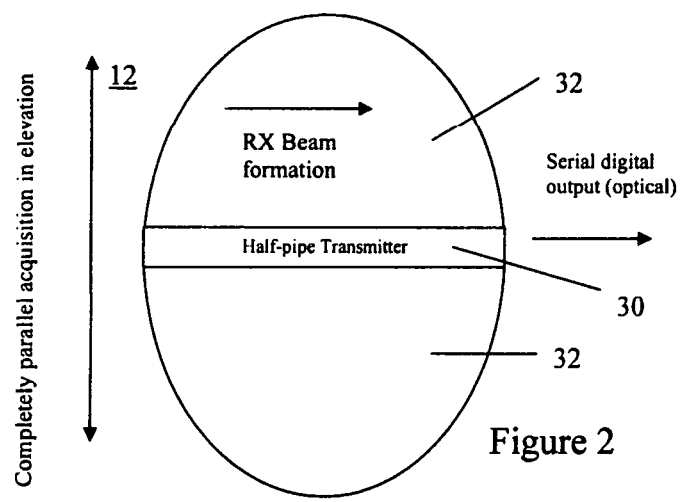
FIGS. 2-5 are graphical representations of transmit and receive apertures and corresponding transducer arrays for generating information for three-dimensional imaging.
Figure 3:
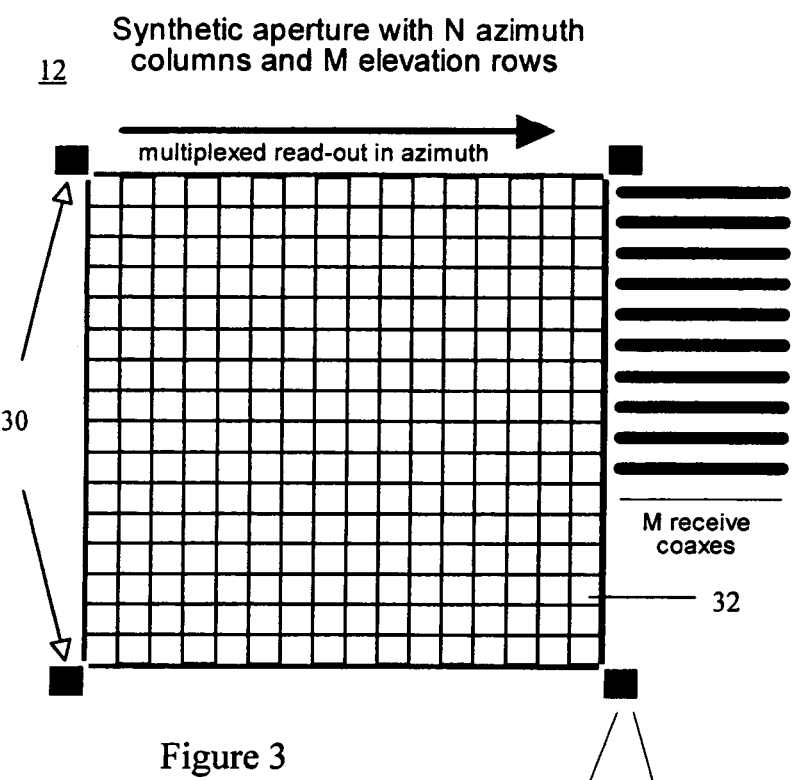
Figure 3:
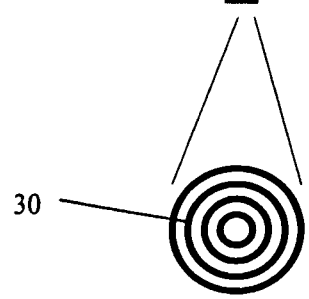

The transmit and receive elements 30, 32 may be the same elements, such as an element being used for transmit also being used for receive. In other embodiments, the transmit elements 30 are separate from the receive elements 32 for a given transmit and responsive receive sequence. The transmit and receive apertures are different. In yet other embodiments, the transmit elements 30 are different devices than the receive elements 32. For example, FIGS. 2 and 3 show different embodiments of the transducer array 12 with separate transmit elements 30 and receive elements 32. The transmit elements 30 are separate from the multi-dimensional array of receive elements 32, such as being separate from the array of receive elements 32 in the two-dimensional grid. The segregation allows for high-power transmitters and high-sensitivity receivers, without compromise to enable transmit and receive operation using the same element. Additionally, piezoelectric transmit elements may be provided under a silicon receiver. The silicon can be thinned by back-grinding so as to minimize the effect of the silicon layer on the transmitter performance.

The segregated transmit and receive elements 30, 32 and/or the divergent scanning provided by the transmit elements provide for co-array or synthetic transmit aperture operation. A co-array is equal to the convolution of the transmit and the receive apertures. The transmit elements for synthetic transmit aperture may be situated on the edges of the array 12 or outside the receive aperture. For example, FIG. 3 shows the transmitters 30 at the corners of a multi-dimensional array of receive elements 32. Four omni-directional elements 30 are positioned at the corners of the fully sampled receive array of elements 32. The transmit elements 30 emit hemispherical waves. The transmit elements 32 are small when compared to a wavelength or are a phased annular array (shown) in which time delays are arranged to defocus the emitted beam. A virtual point source is synthesized.

The receive elements 32 are each independently sampled and used for beamforming. Alternatively, a multiplexed readout conveys the azimuth channels at a given elevation row using one interconnect. The receive elements 32 in each row are independently received by time or frequency multiplexing. A larger number of cables could be provided in order to multiplex fewer channels per cable. Sub-array beamforming, sub-array mixing, or other now known or later developed combinations of information may be used to limit the number of cables.

The transducer array 12 of FIG. 3 may have a resolution equal to that of a traditional imaging aperture of the same size. To achieve exactly the same point-spread function as that aperture, the apodizing function in the synthetic transmit aperture array is set equal to the product of the transmit and receive apodize functions of the traditional array.

FIG. 2 shows another example of segregated transmit and receive apertures. A linear array of transmit elements 30 is spaced along one dimension, such as the azimuth dimension. In one embodiment, the array of transmit elements 30 form a transmitter in the shape of a pipe cut in half along its axis. Rather than a diverging beam in azimuth and elevation, the beam is defocused in one dimension (e.g., elevation) and may be focused in another dimension (e.g., azimuth) with a one-dimensional transmit array of transmit elements 30. Focused scanning is provided in one dimension, but a defocused beam as envisioned in FIG. 2 or a synthetic transmit aperture may be used in another dimension. The large, curved transmit elements 30 may provide more power density.

The receive aperture is split or separated by the transmit elements 30. Separate multi-dimensional arrays of receive elements 32 are provided on each side of the transmit elements 30. While shown as generally oval, other aperture shapes (e.g., square or rectangular) may be provided.

The one-dimensional array of transmit elements 30 provide focus along one dimension. The receive elements 32 in the multi-dimensional pattern may provide for independent operation. To reduce cable count, receive beams focused in azimuth but un-beamformed in elevation are used. The transmit aperture generally forms a plane of acoustic energy focused and/or steered in azimuth, but unfocused in elevation. For each elevation location in the receive aperture, a beam is formed focused and/or steered in azimuth. For a given transmit and receive event, samples representing the insonified plane are output, but without beam formation in elevation.

Figure 4:
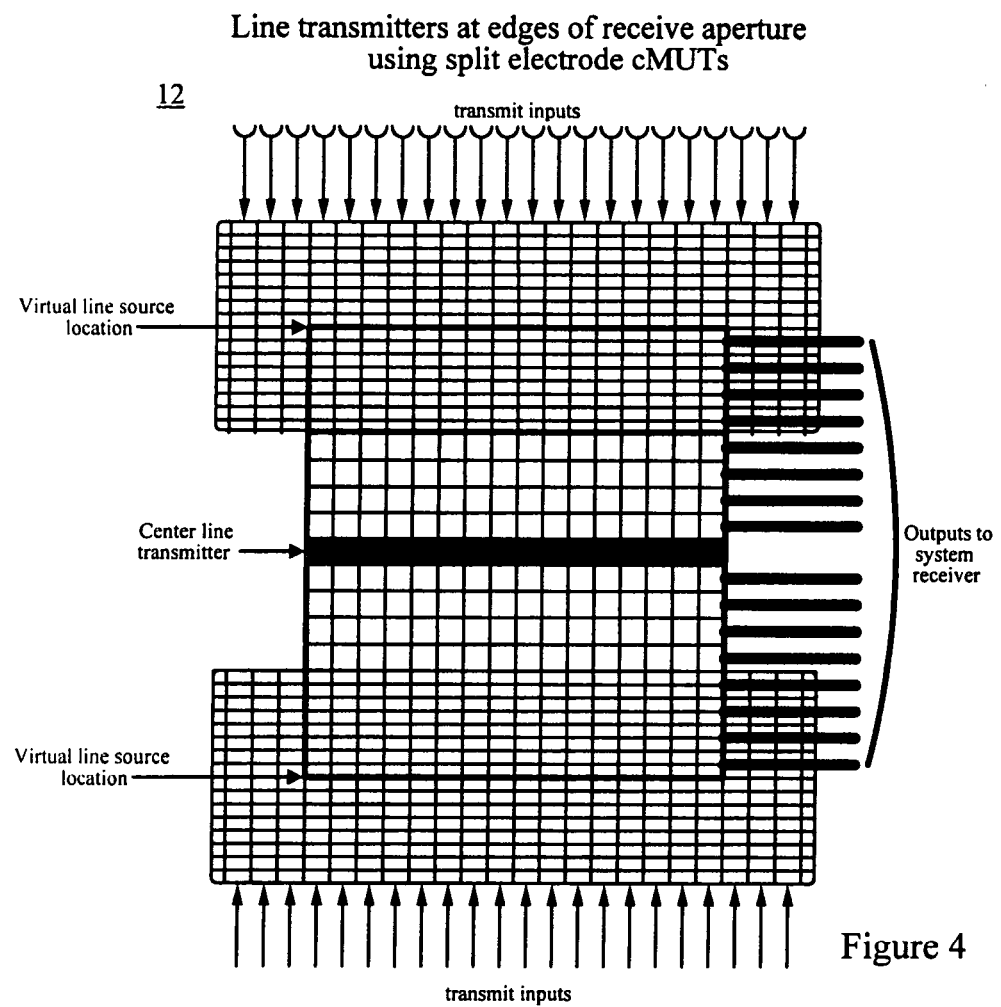

FIG. 4 shows another transducer array 12. Three linear transmitters that are phased in azimuth provide a tight focus at a given point in azimuth, while maintaining a large angular spread in elevation. This arrangement may be considered as a virtual line source. The transmit elements 30 on the edges form two multi-dimensional transmit arrays. For cMUT, bias may be used to focus or steer in the diverging elevation direction, such as disclosed in U.S. Pat. No. 7,087,023, the disclosure of which is incorporated herein by reference. Delays or phasing may alternatively be used. The transmit beams are formed by electronic control to provide the virtual line sources with some or no focus in elevation. Two, or four or more transmit arrays may be provided.

The receive elements 32 include elements can also be used as transmit elements 30. Alternatively, the transmit array is over or beneath the receive array. For example, the transmit array beneath the receive array focuses the acoustic energy along the line at the edge of the receive array. Beyond the receive array, the transmitted energy diverges. In elevation, these transmit apertures are defocused, creating a virtual line source whose origin is at either end of the receive aperture.

Azimuth beams are created by time delaying one of the three transmitters of FIG. 4 to create beams similar to those in a conventional ultrasound scanner. One or more azimuth focal zones are chosen to cover the depth range of interest with sufficient coherence and depth of field. In elevation, the transmit apertures do not form a focused beam. Instead, a diverging, cylindrical wave is created. The elevation aperture is synthesized from three firings, one from the upper line source, one from the center line transmitter, and one from the lower source.

The optional central array of transmit elements 30 may allow for better near-field scanning. A single array or non-virtual line source allows focus in azimuth, such as provided with the virtual line sources. For elevation, the energy is diverging form the face of the transmit elements. Separate from the scanning with the virtual line sources, near field scanning is provided by the center array of transmit elements 30. Multiple transmit events may be used. Alternatively, all three transmit arrays are used to synthesize the elevation aperture, or the transmit arrays are used without synthesis.

For native tissue harmonic imaging (NTHI), the harmonic propagation and/or reflection in response to insonification at a fundamental frequency is detected. However, the harmonic response is weaker than a response at the fundamental. To maximize the transmit power, the bias line defocusing of the virtual line sources may be altered to create a beam converging in elevation as well as azimuth. In such an arrangement, a transmitted intensity similar to that at the focus of a lensed 1D phased array is created.

Figure 5:
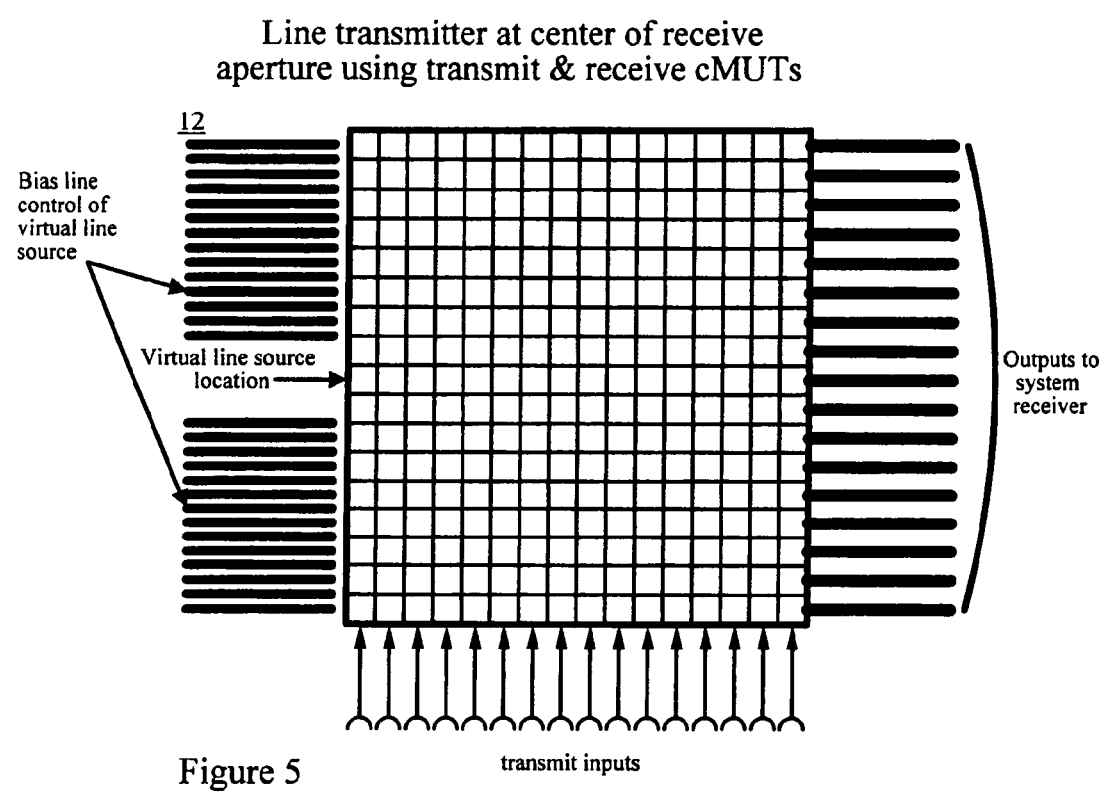

By segregating the transmit and receive elements 30, 32, the complexity of the electronics for scanning may be reduced. However, in some cases, the anatomical window is too small to allow for a transducer that does not employ the entire extent of the array 12 for reception. FIG. 5 shows another embodiment of the transducer array 12 that may use less area. Instead of creating a co-array from a top and bottom line-source firing combined with the receive aperture (see FIG. 4), a virtual line source of transmit elements 30 is provided inside the receive aperture, such as at the center. This may results in some loss of elevation resolution if the spacing of the elevation line sources is reduced.

In a further embodiment, all of the elements of the array 12 are used for transmit and receive. The transmit and receive elements 30, 32 are the same elements. To keep the transmit aperture complexity down, bias line polarity defocusing may be used in the elevation aperture while beam formation focusing is applied to the elements in azimuth. The defocusing in elevation allows for use of synthetic transmit aperture in elevation. The formed virtual line source is located at the center of the elevation aperture, but may be positioned anywhere within the aperture. Alternatively, an integrated transmitter may provide focusing and defocusing delays for each element independently.

FIG. 6 shows one embodiment of the transducer array 12 of FIG. 2 used in a transesophogeal probe. This transducer is an adult transesophogeal (TEE) design with integrated preamplification and azimuth beamforming. The center frequency is 4.5 MHz. Transmit is accomplished by a 64-element curved PZT array 54 producing a traditional focus in azimuth. The PZT array 54 is a half-pipe transmitter. In elevation, the PZT array 54 is curved so that a tight focus is created at or near the surface of the receive cMUT array 52. The transmit beam is defocused in elevation as the sound propagates beyond the surface of the receive array 52.

In FIGS. 2-6, a multi-dimensional grid of receive elements 32 is provided. The elements 32 are provided in an N×M rectangular grid where both N and M are greater than one. The receive elements 32 form a fully sampled receive aperture, but may be used with sparse sampling. The receive aperture may be separated by one or more transmit arrays, such as the receive aperture being on two or more different substrates.

In one embodiment, the receive elements 32 are cMUT elements. The semiconductor substrates used to form the membranes and associated gaps may integrate electronics, such as receive channel circuits containing preamplification, A/D conversion, and beam formation. The maximum amount of information out of the 2D array is desired, such as by providing as little beam formation as possible. With a two dimensional array, some beam formation or signal combination may be used to reduce the data rate or receiver channel density given 2D aperture size and Nyquist spatial sampling. Integrated circuit technology may additionally or alternatively be used to handle the bandwidth and density of wiring involved. Silicon transducers can connect into the chip at integrated circuit density by being manufactured directly on top of the electronics in a monolithic structure. The electronics in the same substrate as the array allows for at least some data compression or beam formation before output to other electronics.

In one embodiment, a preamplifier and sigma-delta analog-to-digital converter is provided for each element in the same substrate, such as directly under each element. The signals are digital when output. Any kind of digital processing to deliver more or less beamforming as required by the application and/or the capabilities of the system may be provided on the same chip or substrate. Bandwidth and dynamic range may be optimized further by providing demodulation in analog before conversion to digital.

In another embodiment, a fully-sampled receive tile of cMUTs in a multi-dimensional grid is provided. The array is built using a low-temperature process that doesn't damage the electronics in the same substrate. The under-cMUT electronics include a preamp, an I/Q mixer to baseband, and sigma-delta A/D including a time varying gain. These electronics are integrated under the corresponding element so that only digital signals traverse the long distances to the side of the aperture or substrate where interconnect or digital processing happens.

Digital processing electronics on the same chip to preserve interconnect density may provide bandwidth reduction to allow for connection to the system by optical or electronic means. This monolithic device (IC+transducer) may be the only active element in the probe, or other chips or circuits are provided in the probe housing. Alternatively, the semiconductor substrates may allow for connection with other semiconductors, such as with flip chip bonding. In other embodiments, PZT type elements are used. Circuits may still be connected on or within the probe housing 10.

Receive channel circuits connect with the receive elements 32. The receive channel circuits apply apodization, delaying, and/or analog-to-digital conversion. In one embodiment, the circuits within the probes shown in U.S. Pat. No. 7,466,256 or 7,583,214, the disclosures of which are incorporated herein by reference, are used. The receive channel circuits are the same or different for each element. For example, the receive channel circuits include the analog-to-digital converters 14, delays, and amplifiers for each receive element. As another example, the signals from the receive elements 32 are conditioned by matching amplifiers which apply gain and bandwidth shaping defined by the input specification of the analog-to-digital converters 14 and the characteristics of the interconnect and on-chip line output amplifier.

The receive channel circuits are within the probe housing 10, such as being in a same semiconductor, a same board, or separate from the array 12. For example, the analog-to-digital converters 14 and/or beamformer 16 are formed in one or more semiconductor chips adjacent to or within the substrate used for the receive elements 32 of the array 12.

The analog-to-digital converters 14 are multi-bit converters sampling at the Nyquist rate or higher. In one embodiment, over sampling converters, such as sigma-delta converters, are used. For example, any of the converters 14 disclosed in U.S. Pat. No. 7,466,256 or 7,583,214, the disclosures of which are incorporated herein by reference, are used. A single converter 14 is provided for each channel, such as for connection with multi-layer PZT receive elements. In other embodiments, a plurality of converters 14 may be provided for each channel, with outboard sample-and-hold circuitry.

The receive channel may also include a bias source for silicon transducers. The bias source is a direct current voltage source, voltage divider, transformer, or other now known or later developed source of fixed or programmable bias. The bias source may include multiplexers. The same or different bias is provided to each element of the receiver aperture. For example, different biases may be applied to provide focusing or defocusing, such as disclosed in U.S. Pat. No. 7,087,023. The bias may also be used for spatial coding in synthesized transmit apertures.

The beamformer 16 may include down converters (e.g., in-phase and quadrature demodulators), amplifiers, delays, phase rotators, summers, over sampling reconstruction filters (e.g., low pass filters), spiking filters, or combinations thereof. For example, one of the beamformers disclosed in U.S. Pat. No. 7,466,256 or 7,583,214 is provided. Down-conversion is provided before or after analog-to-digital conversion. Over sampled data is delayed by selecting a window of single bit data associated with the relative delay. The delayed data is partially reconstructed and decimated. The partially reconstructed data from different channels is then summed for beamformation. The beamformed samples are further reconstructed and decimated, such as decimated to the Nyquist rate.

Other beamformers with or without sigma-delta based conversion may be used. For example, Nyquist sampled values are apodized, relatively delayed, and summed across channels.

The beamformer 16 is operable to at least partially beamform along a first dimension, such as beamforming in azimuth. In the other dimension, such as elevation, the beamformer 16 outputs parallel samplings. Alternatively, partial beamforming (e.g., sub-array beamforming) is provided along multiple dimensions or not performed.

The interface 18 formats the data output by the beamformer 16 for transmission to the imaging system. Data from many elements is multiplexed into a serial optical connection to the imager. Frequency, time, or no multiplexing may be used. Wireless or wired transmission may be used.

Transmit circuits, such as pulsers, waveform generators, switches, delays, phase rotators, amplifiers, and/or other devices, are within the probe housing 10. Control signals from an imaging system control operation of the transmit circuits. Alternatively, the transmit waveforms are generated outside the probe housing.

The data is output from the probe housing 10 wirelessly or on one or more wires (e.g., coaxial cables or a bus). The data is stored in the memory 20. The memory 20 is a dual ported RAM or other memory. The data corresponds to three-dimensions—azimuth channel, elevation channel and sample number.

The processor 22, such as an array of digital signal processors, beamformer, field programmable gate arrays, or general processor, completes the beam formation function. For example, beam formation using synthetic transmit aperture processing in the elevation dimension is performed. Further beam formation in the azimuth dimension may also be provided. The beamforming is provided by specialized beamforming hardware and/or by software. Beamforming under software control may not require a custom beamforming ASIC, and may more easily allow introduction of new algorithms without a costly and time-consuming ASIC redesign. Such algorithms can operate either in beam space or channel space, and run the gamut of high-value additions to the simple beamforming and flow imaging. Aberration correction, correlation functions for motion correction, strain imaging and vector flow, beam-to-beam filtering for super-resolution, or adaptive artifact canceling may be provided.

The data output from the processor 22 is stored in the memory 24, such as a cache, system memory, hard drive, optical media, graphics memory, or other memory. The data is represents beams, such as an array of data with axes of azimuth beam, elevation beam and sample number. The output beamformed data may alternatively be in a Cartesian coordinate format.

The display processor 26 is a graphics processing unit, general processor, digital signal processor, or other processor for rendering. The processor 26 may convert the data into a Cartesian coordinate system or render from the polar coordinate formatted data. Three-dimensional rendering is performed, such as by surface rendering or projection (e.g., maximum intensity projection). Other types of imaging may be provided, such as two-dimensional imaging or cut-planes at arbitrary angles. Other processes may be provided, such as segmentation, speckle reduction, or other filtering.

Referring again to FIG. 6, one embodiment of the transducer array 12 for use with synthetic transmit aperture in elevation and beamforming in the probe housing 10 for azimuth is shown. The transmit and receive arrays 52, 54 are operable at a center frequency of 4.5 MHz. The aperture diameter of the receive arrays 52 is about 9.6 mm. The element width is 0.6 wavelengths. The maximum imaging depth is 160 mm.

The number of cables between the probe housing and the imaging system is determined by the receive multiplexing. 64 connect the system to the curved half-pipe. The transmitter may also be used for reception to avoid a gap in the spatial sampling of the returning acoustic wave. The transmit array is a half pipe of 64 elements spaced in azimuth. The elements are shaped as shown (e.g., quarter circles) to create a line source at the tip or face of the array. For a 48×48 receive array, 2,304 receive elements are provided. Elements on the edges, such as at the corners, may be discarded or not used to reduce the number of receive elements, such as reducing to 1,666 receive elements.

Using the beamforming described herein, 64 transmit events are provided to scan a volume for receiving a single azimuth beam for each transmit event (i.e., the transmit covers a plane at one azimuth angle for reception of beams within that plane at the azimuth angle). That is, the transducer acquires a slice in the time a traditional probe takes to acquire a beam. Two or more azimuth beams may be received in response to each transmit event, such as receiving for two or more (e.g., 4) azimuth planes or angles. For example, the receive channels may form four azimuthally spaced beams for each transmit to decrease the time for scanning. The 1,666 receive elements are grouped into sub-apertures for azimuth beamforming within each sub-aperture. Each sub-aperture comprises a subset of the total aperture, for example a line of elements horizontally oriented in FIG. 2. This produces 48 digital outputs. Other sub-aperture schemes are possible. Sub-aperture beam formation occurs in the probe housing. Channel data is output in elevation as the results of partial beamforming of each sub-aperture. The beamforming in azimuth is provided at the array 12 to reduce bandwidth. Elevation beamforming is provided in the imaging system. The resolution is independent of depth in elevation.

292 volumes may be scanned per second for B-mode imaging. For color or flow imaging with 8 firings (pulse repetitions per estimate) over ½ of the transmit aperture, the volume may be scanned 73 times per second. Such scan rates may allow substantially real-time cardiology imaging in three dimensions.

Channel data rather than partially beamformed data may be output. For example, azimuth channel data from prior to azimuth beamforming is also output. Two-dimensional aberration correction may use the azimuth channel data. Since elevation beamforming may not occur in the probe housing, elevation channel data may also be available for aberration correction.

The embodiment of FIG. 6 also shows optional cooling pipes 50, 56. A gas, liquid, or other substance cools the electronics and transducer array 12. The wedge shaped substrate of the receive arrays 52 assists in focusing the transmit energy as a line source, includes the converters 14 and beamformer 16, and has the receive arrays 52. These structures may be cooled for operation that meets regulatory requirements.

FIG. 6 as described above provides a specific embodiment. Other embodiments may have the same or different characteristics.

In one embodiment, a substantially fully sampled two-dimensional array of capacitive membrane ultrasound transducers is used for imaging. Beamforming is performed in azimuth for the two-dimensional receive aperture. In elevation, the transmit aperture is synthesized. Synthesis of the transmit aperture corresponds to using a sparse transmit aperture, such as point or lines, for transmission with reception in an area. Any transmit aperture synthesis may be used, such as disclosed by R. T. Hoctor and S. A. Kassam, *The unifying role of the coarray in aperture synthesis for coherent and incoherent imaging*, published in IEEE Proc., 78(4), 735-752 (1990); by F. Ahmad and S. A. Kassam, *Coarray analysis of wideband pulse-echo imaging systems*, 1996 IEEE International Conference on Acoustics, Speech, and Signal Processing, 6, 3185-3188; by G. R. Lockwood and F. S. Foster, *Optimizing sparse two-dimensional transducer arrays using an effective aperture approach*, published in Proceedings of the IEEE Ultrasonics. Symposium, 1497-1501 (1994); by S. Nikolov and J. A. Jensen, *Application of different spatial sampling patterns for sparse-array transducer design*, Ultrasonics 37(10), 667-671, (2000); in EP1300690/WO0068931; or EP1194920/WO0068931. Other transmit aperture synthesis may be used for the elevation or other dimensions.

In one embodiment, a transmit firing acquires a 2D data set—an elevation plane—at a single azimuth angle. MZ beams create a volume with focal zones, Z, making the imaging speed about 50/Z volumes per second. High-speed volume acquisition may assist in cardiology diagnosis or other medical imaging applications. Using synthetic transmit aperture imaging along one dimension may provide focus throughout the acquired volume, make all the information that can be extracted from the tissue given the transducer's aperture and bandwidth available, and may enable various advanced signal processing methods.

Figure 7:
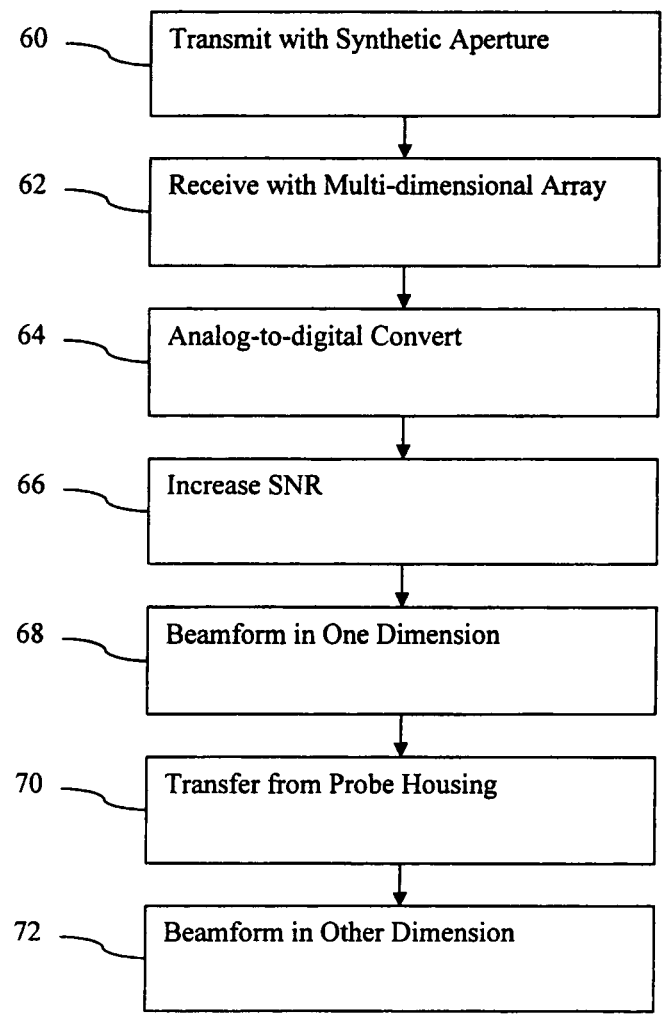
FIG. 7 is a flow chart diagram of one embodiment of a method for generating ultrasound information for three-dimensional imaging.

FIG. 7 shows a method for generating ultrasound information for three-dimensional imaging. The method is implemented using the system of FIG. 1 or a different system. The method uses the transducer arrays 12 of FIGS. 2-6 or different transducer arrays. Different, fewer, or additional acts may be provided. One or more acts performed in the transducer probe housing (e.g., 60-70) may be performed in the back-end system. The acts are performed in the order shown or a different order.

In act 60, acoustic energy is transmitted. The acoustic energy is substantially unfocused along at least one dimension for synthetic transmit aperture processing. "Substantially unfocused" is a diverging beam from a shallowest depth to be imaged, a plane wave, or beam shape covering many scan lines (e.g., 10 or more). The acoustic energy may be focused in other dimensions, such as azimuthally focused along one or more (e.g., up to 4) azimuthally spaced scan line or planes. The focus is within the region to be imaged. The different dimensions are orthogonal in one embodiment (e.g., azimuth and elevation) or non-orthogonal, such as being at an acute angle to each other.

The transmission is generated in response to an electric waveform being applied to at least one element. Different or the same waveforms may be applied to a plurality of elements. The waveforms may be relatively timed and apodized to provide the desired focus or lack of focus. Alternatively or additionally, the size or number of elements of the transmit aperture with or without a lens provides the desired focus or lack of focus.

In one embodiment, a half pipe transmit aperture provides a diverging beam shape along one dimension. An array of elements along another dimension allows focusing. In other embodiments, individual transmit elements or small arrays of transmit elements generally insonify a volume to be imaged. The insonification may be focused in a sharp beam, a defocused beam, or in a plane in any direction, or unfocused.

The transmission is performed one time for an entire volume. In other embodiments, the transmission is performed multiple times for the entire volume. The transmissions may be repeated one or more times for each of a plurality of sub-regions within the volume, such as transmitting one or more times for each of a plurality of planes stacked along the azimuth dimension.

In act 62, acoustic echoes are received in response to the transmitting. The echoes return from the region subjected to the transmit beam. Since the transmit beam is unfocused along at least one dimension, the region is at least a planar region, but may be a volume. The reception is performed for each transmission, so may be repeated for a same or different volume or sub-region.

The reception is performed with a multi-dimensional transducer array. In one embodiment, the array is of microelectromechanical elements, such as a cMUT array or other small or nano-scale structures with electrical interaction. The array is substantially fully sampled, such as a receive aperture split into two halves by a transmit linear array where each half is fully sampled. The elements of the array transduce from the received acoustic energy into electrical signals.

In act 64, the electrical signals from the receive elements are converted to digital signals. In one embodiment, sigma-delta conversion is performed, but other conversion may be provided. Sigma-delta conversion outputs single bit samples, but multi-bit samples may be provided. Only one conversion is performed for each element in one embodiment, but multiple or parallel conversions for each receive element may be provided to increase dynamic range.

The conversion occurs before or after amplification. The amplification provides receive signals more likely above a noise level. The amplification and/or the conversion may include a time varying level for depth gain compensation. In one embodiment, the feedback level within a sigma-delta converter varies as a function of time for implementing at least a portion of the depth gain compensation. Digital or analog amplification may be used.

The digital signals output after conversion and any filtering are beamformed and synthesized. The beamforming is partial, or performed for less than the entire aperture. For example, beamforming is provided in act 68 along one dimension, such as in azimuth. For another dimension, synthetic aperture transmit is used. The beamforming provided for this dimension is performed separately from or after beamforming along the first dimension.

In act 66, the signal-to-noise ratio of the synthesizing may be increased by spatial transmit coding, temporal coding prior to beamforming, compensating for motion, or combinations thereof. Since the transmit aperture may be smaller and/or separate from the receive aperture, the noise level may be greater than for a more focused transmit beam. While a volume of data may be acquired in a lesser number of firings (e.g., in just one firing of each of four transmitters shown in FIG. 3 or in one or more firings for each azimuth plane for the transmitter shown in FIGS. 2 and 6), the signal-to-noise ratio may be less due to the breadth of the transmitted energy. If an imager has an aperture of area $A_T$, and the area of each defocused transmitter is $A_D$, the emitted power decreases by a factor of $A_T/A_D$. Moreover, the focusing gain of the transmit aperture is lost. These effects, when combined, can provide a 30 dB loss of signal.

In one embodiment, the signal-to-noise ratio is increased by spatial encoding. The transmit energy is increased by transmitting from different transmit apertures at the same time, such as transmitting from the four transmit arrays of FIG. 3. Any spatial encoding may be used, such as disclosed in U.S. Pat. Nos. 5,851,187 and 6,048,315, the disclosures of which are incorporated herein by reference. Without coding, the image may be formed by a summation of the data from each of the four transmit elements 30 on separate firings of FIG. 3. Spatial coding allows transmission with all four transmit elements 30 at once, possibly recovering 6 dB of signal-to-noise ratio. Four firings are still used, but the acoustic energy from each element is different in phase, polarity, or other coding matrix. Signal processing of the received signals separates out the reflections associated with the different transmit elements 30. The decoding is multiplication of the data by the inverse of the coding matrix. One matrix is a Hadamard matrix.

In another embodiment, temporal coding is used to increase the signal-to-noise ratio. Pulse compression (i.e., the use of transmit codes with long time-bandwidth products) allows separation of the signals from different transmit elements 30. Various coding schemes, such as chirps, Golay codes and Barker codes, may be used. By performing the "spiking filter" or inverse of the code operation on channel data prior to beam formation, longer time-bandwidth products can be achieved, with concomitant improvement in signal-to-noise ratio. The inverse may be applied after beam formation or partial beam formation for a lower cost solution. A lack of time invariance may limit achievable time-bandwidth product.

In another embodiment, the signal-to-noise ratio is increased by varying the bias of cMUT transducers for spatial coding. If a multi-firing multiplexed transducer (see FIG. 5) or other cMUT transducer array is used, signal-to-noise ratio can be gained using a cMUT-specific, receive-only implementation akin to the spatial transmit coding. Instead of receiving from a certain element that is selected by an on-chip MUX, a group of elements is selected. To illustrate, consider a 2×2 matrix of elements. Over four firings, the bias polarities are switched in a pattern so that linear combinations of the received data recreate the signal from each element. For example, Hadamard coding may be used. There is no increase in acquisition rate, since four firings would be used to collect the data in the MUX-only case. For each firing, four times the receive area is active, resulting in a 6 dB SNR gain. Larger processing gains may be obtained from choosing larger sub-apertures.

In another embodiment, signal-to-noise ratio is increased by motion compensation. The data from sequential transmitter firings is coherently combined, yielding $10 \log_{10} F$ dB of improvement if F is the number of firings added. For F>4 (approximately), tissue motion is estimated to preserve coherence. For multiple firings, the coherence between data should be maintained over the entire volume because each firing contributes to the complete volume, and not just to a single beam as in a beam-by-beam scanner.

Tissue motion is determined by correlation, such as searching for a best match using the minimum sum of absolute differences. Other motion estimation techniques may be used, such as cross-correlations between the data sets. The data is shifted to counteract the motion between transmit events prior to combination. The lateral motion may be estimated by the zero-lag autocorrelation method.

Combinations of techniques may be used. In other embodiments, additional processes to increase signal-to-noise ratio are not provided.

In act 68, receive beamforming is provided. The receive beamforming is complete for the entire aperture in one embodiment. In other embodiments, the receive beamforming is partial, such as beamforming within each of a plurality of sub-apertures. Another example of partial beamforming is beamforming along one dimension for receiving in a multi-dimensional array. Relative delays and apodization are applied along one dimension, such as azimuth, or some other shape of sub-aperture is configured such as a rectangle or hexagon. The relatively delayed and apodized receive signals are summed. The beamforming along the dimension focuses and/or steers the receive beam along the dimension. In the other dimension, no or different beamforming is provided. Each elevation spaced beamformed output corresponds to samples for a two-dimensional plane extending along a second dimension (e.g., elevation) at the steered angle in one example.

In one embodiment, partial receive beamforming is performed in azimuth with spaced sub-arrays of elements. Each sub-array corresponds to a line of elements extending in the focus direction (e.g., azimuth). More than one line of elements may be included in one or more sub-arrays. The sub-arrays each extend along the entire azimuth extent of the receive aperture. Alternatively, a plurality of sub-arrays is spaced along azimuth.

The partial receive beamforming is performed by circuits in the transducer probe. The beamforming is analog or digital. For digital beamforming, the electrical signals are converted with sigma-delta, over sampling, or multi-bit converters.

In act 70, the beamformed signals are transferred to an imaging system, computer or other device from the probe housing. The transfer is over separate cables, such as one for each sub-array beam sum. In other embodiments, the transfer is over a bus, multiplexed for serial transmission, or wirelessly transmitted. Due to the partial beamforming, the amount of data to be transmitted from the multi-dimensional receive aperture is reduced. Alternatively, further processing, such as the beam formation in the other dimension, is performed in the probe housing for further data reduction.

In act 72, complete beam sums are determined. The data output from sub-arrays is relatively delayed and apodized. The resulting samples are summed. With elevation sub-arrays and previous partial beamforming in azimuth, the beamforming is performed along the elevation dimension.

The imaging system, such as the computer, separate from the transducer probe performs the beamforming. Since channel data in the form of partial beamforming along one dimension is provided, channel related processes may be performed prior to beamforming. The elevation aperture is synthesized.

The multi-stage beamforming is digital. Digital reconstruction is provided for three-dimensional imaging of a volume in real-time. The beamformed data is rendered. For example, the data is interpolated or transformed to an evenly spaced grid. The data is rendered by projection or surface rendering. Two-dimensional imaging may alternatively be provided.

While the invention has been described above by reference to various embodiments, it should be understood that many changes and modifications can be made without departing from the scope of the invention. As used herein, "connected with" includes direct or indirect connection. For example, one or more hardware or software components may be between two connected components.

It is therefore intended that the foregoing detailed description be regarded as illustrative rather than limiting, and that it be understood that it is the following claims, including all equivalents, that are intended to define the spirit and scope of this invention.

We claim:

1. A method for generating ultrasound information for three-dimensional imaging, the method comprising:

transmitting acoustic energy substantially unfocused along a first dimension and focused along a second dimension different than the first dimension, the focused acoustic energy including a focus within an image region such that the transmission covers no more than four scan lines along the second dimension and the unfocused acoustic energy of the transmission covers ten or more scan lines along the first dimension;

receiving, in response to the transmitting, with a multi-dimensional transducer array;

initially beamforming in azimuth and not elevation for a two-dimensional receive aperture; and synthesizing a transmit aperture in elevation from an output of the beamforming.

2. The method of claim 1 wherein receiving comprises acquiring a set of data representing an elevation plane at an azimuth angle from a single transmit, and wherein beamforming comprises beamforming the data.

3. The method of claim 1 wherein beamforming comprises beamforming with a substantially fully sampled two-dimensional array of capacitive membrane ultrasound transducers.

4. The method of claim 1 wherein beamforming comprises partial beamforming in azimuth spaced sub-arrays, the partial beamforming within a transducer probe, and wherein synthesizing comprises synthesizing in elevation within an imaging system separate from the transducer probe.

5. The method of claim 1 wherein transmitting comprises repetitively transmitting acoustic energy substantially unfocused along elevation and focused along azimuth, and wherein receiving comprises repetitively receiving, in response to the transmitting, with a substantially fully sampled two-dimensional array of microelectromechanical elements.

6. The method of claim 1 further comprising:

sigma-delta analog-to-digital converting received electrical signals, the beamforming and synthesizing operating on the converted electrical signals.

7. The method of claim 1 wherein the transmitting comprises transmitting from a half-pipe transmit aperture, and wherein receiving comprises receiving with a substantially fully sampled two-dimensional array of elements in a split receive aperture, the split receive aperture being across the half-pipe transmit aperture.

8. The method of claim 1 further comprising:

increasing a signal-to-noise ratio of the synthesizing by spatial transmit coding, temporal coding prior to beamforming, compensating for motion, or combinations thereof.

9. The method of claim 1 wherein beamforming and synthesizing are responsive to data received with a two-dimensional array of capacitive membrane ultrasound transducers; further comprising:

spatial coding by varying biases of the transducers.

10. An ultrasound transducer array for medical diagnostic ultrasound imaging, the transducer array comprising:

a probe housing;

a two-dimensional grid of capacitive membrane ultrasound transducer elements on or within the probe housing;

a plurality of receive channel circuits connected with the elements and operable to at least partially beamform along a first dimension, the receive channel circuits within the probe housing; and at least one transmit element separate from the elements of the two-dimensional grid, the transmit element configured to generate a beam substantially unfocused along a second dimension different from the first dimension and focused, with a focus within an image region, along the first dimension such that the beam covers less than five scan lines along the first dimension and covers ten or more scan lines along the second dimension.

11. The transducer array of claim 10 wherein the receive channel circuits are configured to output samplings along parallel lines in the second dimension.

12. The transducer array of claim 10 wherein the at least one transmit element comprises a plurality of elements outside a receive aperture of the transducer elements.

13. The transducer array of claim 10 wherein the at least one transmit element comprises a piezoelectric element.

14. The transducer array of claim 10 wherein the at least one transmit element comprises a half-pipe transmitter.

15. The transducer array of claim 10 wherein the at least one transmit element comprises a linear array of transmit elements spaced along the first dimension, and wherein the two-dimensional grid is separated by the linear array.

16. The transducer array of claim 10 wherein the receive channel circuits comprise sigma-delta analog-to-digital converters.

17. The transducer array of claim 10 wherein the receive channel circuits comprise a bias source operable to vary bias polarities for spatial coding.

18. A method for generating ultrasound information for three-dimensional imaging, the method comprising:

transmitting acoustic energy substantially focused, with a focus within an image region, along a first dimension and substantially unfocussed along a second dimension different than the first dimension such that the acoustic energy covers only four or fewer scan lines out of at least one hundred along the first dimension;

partial receive beamforming, in sub-arrays of elements, first data generated in response to the transmitting, the partial receive beamforming forming second data representing a two-dimensional plane extending along the second dimension at an angle in the first dimension; and then beamforming the second data along the second dimension.

19. The method of claim 18 wherein partial receive beamforming comprises partial receive beamforming within a transducer probe, and wherein beamforming comprises beamforming in an imaging system separate from the transducer probe.

20. An ultrasound transducer array for medical diagnostic ultrasound imaging, the transducer array comprising:

a probe housing;

a multi-dimensional grid of capacitive membrane ultrasound transducer elements on or within the probe housing, the elements on or in a substrate;

a plurality of sigma-delta analog-to-digital converters on or in the substrate;

a plurality of mixers on or in the substrate and electrically connected between the elements and the converters; and a plurality of receive channel circuits connected with the converters and operable to at least partially beamform along at least a first dimension, the receive channel circuits in the probe housing.

21. The ultrasound transducer of claim 20 further comprising a plurality of preamplifiers on or in the substrate and electrically connected between the elements and converters.

22. The ultrasound transducer of claim 20 wherein the receive channel circuits are on or in the substrate.

23. The ultrasound transducer of claim 20 wherein the elements are fully sampled in the multi-dimensional grid.

* * * * *